United States Patent
Ondov et al.

(10) Patent No.: US 6,732,569 B2
(45) Date of Patent: May 11, 2004

(54) SYSTEM AND METHOD FOR COLLECTING SAMPLES OF ATMOSPHERIC AEROSOL PARTICLES FOR NEAR-REAL TIME ANALYSIS

(75) Inventors: John M. Ondov, Clarksville, MD (US); Christopher B. Kidwell, Sterling, VA (US); Thomas M. Tuch, Leipzig (DE)

(73) Assignee: University of Maryland, Riverdale, MD (US)

( * ) Notice: Subject to any disclaimer, the term of this patent is extended or adjusted under 35 U.S.C. 154(b) by 0 days.

(21) Appl. No.: 10/054,874

(22) Filed: Jan. 25, 2002

(65) Prior Publication Data

US 2002/0134137 A1 Sep. 26, 2002

Related U.S. Application Data

(60) Provisional application No. 60/263,930, filed on Jan. 25, 2001.

(51) Int. Cl.⁷ .................................................. G01N 1/00
(52) U.S. Cl. ........................ 73/28.05; 73/28.01; 73/23.2
(58) Field of Search ............................... 73/23.2, 28.01, 73/28.05; 95/216, 149, 230, 237; 356/312, 326, 315; 422/100, 68.1, 73

(56) References Cited

U.S. PATENT DOCUMENTS

| | | | | |
|---|---|---|---|---|
| 4,141,701 A | * | 2/1979 | Ewan et al. | 95/217 |
| 5,095,205 A | | 3/1992 | Schleicher et al. | 250/226 |
| 5,176,723 A | | 1/1993 | Liu et al. | 95/216 |
| 5,320,051 A | * | 6/1994 | Nehls, Jr. | 110/345 |
| 5,708,502 A | | 1/1998 | Denton et al. | 356/312 |
| 6,284,022 B1 | | 9/2001 | Sachweh et al. | 95/149 |
| 6,386,015 B1 | * | 5/2002 | Rader et al. | 73/31.05 |
| 6,431,014 B1 | * | 8/2002 | Liu et al. | 73/863.22 |
| 6,506,345 B1 | | 1/2003 | Lee et al. | 422/100 |

* cited by examiner

Primary Examiner—Hezron Williams
Assistant Examiner—Rodney T. Frank
(74) Attorney, Agent, or Firm—Rosenberg, Klein & Lee (57) ABSTRACT

A system and method for collecting sub-hourly ambient particulate matter samples at flow rates of 170–260 L/min is suitable for either on- or off-line near-real-time multielement analysis by graphite furnace atomic absorption spectrometry and other techniques for which a sample in slurry form is advantageous. Condensational growth of water vapor was used to grow fine particles by steam injection. The grown droplets are concentrated using a virtual impactor, then separated from the airstream using a real impactor. The particles are collected in a liquid slurry which is hydraulically delivered to sample vials every 30 minutes for offline analysis, or directly delivered into the graphite furnace for atomic absorption spectrometry analysis.

22 Claims, 5 Drawing Sheets

SYSTEM AND METHOD FOR COLLECTING SAMPLES OF ATMOSPHERIC AEROSOL PARTICLES FOR NEAR-REAL TIME ANALYSIS

REFERENCE TO RELATED PATENT APPLICATION

The subject Utility Patent Application is based on a Provisional Patent Application No. 60/263,930 filed Jan. 25, 2001.

This invention was made with Government support under Contract EPAR825269010 awarded by the Environmental Protection Agency (EPA). The Government has certain rights in this invention.

FIELD OF THE INVENTION

The present invention relates to chemical analysis of the elemental composition of atmospheric aerosol particles and, more particularly, to a system and method for collecting sub-hourly ambient aerosol for elemental and chemical analysis.

The present invention also relates to the automated sampling of ambient aerosol particles in a manner suitable for multi-element analysis of collections made at sub-hourly intervals with commonly available laboratory analysis instruments, wherein the samples are collected with sufficient efficiency to be regarded as quantitative.

Even more particularly, the present invention relates to a system and method which allows removal of aerosol particles from ambient air introduction of them into an aqueous slurry at a concentration suitable for analysis by a broad range of off-the-shelf analytical instrumentation for elemental and chemical compound or chemical ion analysis, as well as for toxicological testing.

The present invention further relates to a monitoring system and method for determination of trace elements and heavy metals in ambient aerosol particles where the collected samples may be stored either in a series of vials for off-line analysis and testing without interfacing problems, or can be introduced directly into analytical instruments for near-real-time on-line analysis.

BACKGROUND OF THE INVENTION

Measurements of airborne concentrations of major, minor, and trace elements are clearly needed for assessments of human health risk, environmental contamination, compliance with National Air Quality Standards (NAAQS), and source attribution by receptor modeling techniques. Important issues include improvements in the characterization of the temporal history of aerosol exposure and in the linkage of the levels of aerosol particles and their toxic constituents to their sources, i.e., improved source-receptor relationships. Some states, including Maryland are considering continuous source monitoring for toxic air pollutants.

With regard to health risks, residental, workplace, and ambient outdoor environments are of interest. Most elements of environmental interest reside on aerosol particles, usually those with diameters smaller than 10 μm. Elements of interest include Pb (a criteria pollutant); elements listed as "air toxins", e.g., Cd, Cr, Cu, Ni, As, Se, and Hg; essential nutrients, e.g., Fe; and those toxic to marine organisms, e.g., Al. Elements of interest to the receptor modeling community include all of the aforementioned and much of the rest of the periodic table. Since many elements must be determined simultaneously, requirements for receptor modeling are perhaps the most demanding. Average concentrations of these elements in the urban and rural areas usually are of the order of 0.1 ng/$m^3$ for Cd, Co, and Ag; 1 to 5 ng/$m^3$ for As, Cr, Mn, Pb, Se, and V, about 10 ng/$m^3$ for Ti and Zn; and 100 ng/$m^3$ for Al and Fe.

At the above-mentioned concentrations, continuous or even near-continuous monitors are virtually nonexistent. Instead, air sampling for elemental analysis typically involves preconcentration of the aerosol by filtration or impaction, followed by off-line analysis by highly sensitive analytical techniques such as X-ray fluorescence (XRF), instrumental neutron activation analysis (INAA), atomic spectroscopy techniques (atomic absorption and atomic emission), and mass spectrometry (e.g., inductively-coupled plasma-mass spectrometry, ICPMS). This is generally performed with dichotomous and impactor samplers which size-fractionate aerosol particles (thereby increasing required analytical sensitivity) and can accommodate low-mass, low-blank substrates, e.g., Gelman "Teflo" PTFE filters. Standard samplers use 47- or 37-mm substrates and typically operate at from 17 to 40 L/min, although a flow rate of 80 L/min is achieved with 47-mm "Teflo" filters in the UMCP dichotomous sampler (Wu, et al. "Chesapeake Bay Atmospheric Deposition Study, Year 1: Sources and Deposition of Selected Elements in Aerosol Particles", Atmos. Environ, 28:1471–1486, 1994). As a result, sample collection times, as long as 6–24 hours, are much longer than time scales for changes in source strengths and important meteorological parameters, e.g., wind direction, mixing height, temperature, and relative humidity (RH).

Multi-elemental analysis is often performed first by a conventional energy-dispersive (ED) XRF technique, followed by INAA. The two techniques are complimentary and can provide concentrations for more than 40 elements in typical air samples. The XRF technique provides good sensitivity for Pb, Cu, Ni, S, and Si, i.e., elements which are not readily detected by INAA while INAA provides many more elements for which XRF is insensitive, e.g., V, As, Se, Sb, and rare earths. However, neither technique routinely provides Cd data in typical air samples. In Maryland (where the average airborne Cd concentration is only about 0.1 ng $m^3$), the far superior performance of Graphite-Furnace atomic absorption (with Zeeman background correction) is routinely used for Cd analyses. This is accomplished subsequent to sample dissolution and removal of silica and carbon using nitric, perchloric, and hydrofluoric acids. With this type of methodology, multi-elemental analyses are greatly time consuming and, thus, expensive, which makes high temporal resolution often impractical, simply from the standpoint of analytical costs. Additionally, when samples are dissolved prior to analysis by GFAA, only a small fraction of the sample (typically 5 to 20 μL) is introduced into the furnace. To overcome this deficiency, techniques have been devised for introducing atmospheric particulate matter directly without dissolution, thus reducing air sampling requirements substantially.

As described in Sneddon ("Direct collection of lead in the atmosphere by impaction for determination by electrothermal atomization atomic absorption spectrometry," Anal. Chem., 56:1982–1986, 1984; "Use of an impaction-electrothermal atomization atomic absorption spectrometric system for the direct determination of cadmium, copper, and manganese in the laboratory atmosphere," Anal. Letters, 18:1261–1280, 1985; "Direct and near real time determination of metallic compounds in the atmosphere by AA", American Laboratory, 18 (3): 43–50 1986; "Direct and near real-time determination of metals in the atmosphere by atomic spectroscopic techniques," Trends in Anal. Chem., 7:222–226, 1988; "Collection efficiency of an impaction-electrothermal atomization atomic absorption spectrometric system for the direct and near-real-time determination of metals in aerosols: some preliminary results," Appl. Spectrosc., 43:1100–1102, 1988; and "Multielement atomic absorption spectrometry, a historical perspective," Microchem J., 48:318–325, 1993) a single, tantalum-jet impactor was designed to fit in the sample introduction port of a graphite furnace platform. An air-tight container was used to house the platform during sample collection. Sampling rates were limited by the small size of the 8-mm-id platform thus limiting the ability to aspirate ambient aerosol at rates only up to 15 L/min. After collection, the platform was removed from the sample collection housing and placed in the furnace for single-element analysis of the sample.

Sneddon reported detection limits in $ng/m^3$ for 17 elements including Cr, Co, Fe, Ni, Pb, Se, Si, Sn, and Zn based on direct, sequential, single-element analysis of aerosol particles collected for 5 min at an air flow rate of 10 L/min using an Instrumentation laboratory 457 AA with model 655 graphite furnace. Sneddon's detection limits are the concentration giving a signal-to-noise ratio of 3. Except for Zn and Fe, these detection limits exceed ambient concentrations by from 10- to 20-fold, indicating that samples would need to be collected for from about 50 to 100 minutes to achieve analyses at the detection limit for elements occurring in the atmosphere at their average concentrations; while concentrations less than the average would not be detected. To achieve analyses at the detection limit when sampling the minimum concentrations of all detected elements (except Fe and Zn), sampling times would have to be increased from 2 to 32 hours and only one element could be obtained in the sample.

As an alternative to the direct GFAA technique of Sneddon, Chakrabarti, et al. ("Direct determination of metals associated with airborne particulates using a graphite probe collection technique and graphite probe atomic absorption spectrometric analysis," Spectrochimica Ata., 42B: 1227–1233, 1987), developed another off-line sampler consisting of a rectangular porous graphite probe (25-mm long, 5-mm wide, 0.2 mm thick) which could be mounted in a modified filter holder to collect ambient aerosol particles at a flow rate of 0.1 L/min. After sampling, the probe was removed from the holder and inserted into the graphite furnace platform and analyzed using a Perkin-Elmer model 5000 AA, with a model HGA-500 graphite furnace. Detection limits in $ng/m^3$ were reported for Pb, Cd, Cu, Ni, Mn, Zn, Cr, and V at sampling times ranging from 1.4 to 3440 minutes. For the elements such as Cr, Ni, Pb, and Zn, the detection limits were from 3-(Zn) to 30-(Pb) fold lower than those achieved by Sneddon's instrument. Some of these differences may be attributable to differences in the method of calculating detection limits.

As described by Miller-Ihli ("*Solid Analysis by GFASS,*" *Anal. Chem,* 64, 964A–968A, 1992), direct solids analysis by GFAA, has been successfully applied to a large number of sample matrices, owing largely to recent advances in furnace technology and application of Zeeman-effect background correction. Zeeman background correctors use a powerful magnetic field to effect hyper-fine splitting of the incident line source into multiple components other than the analytical wavelength. Broadband molecular absorption and scattering losses are measured while the field is on, atomic absorption is measured at the analyte wavelength when the field is switched off. In addition to airborne particles, relevant matrices include biological samples of coal, coal fly ash (As, Cd, Cr, Hg, and Ni) and waterborne suspended particulate matter. Many solid materials have been analyzed after preparing a slurry (usually in dilute nitric acid) to permit volumetric introduction into the graphite furnace, e.g., with a pipette or auto sampler. Detection limits reported for direct analyses of slurry samples are comparable to those obtained by Chakrabarti, et al.

In the multi-element GFAA analysis with direct sample injection, the entire sample is consumed during the analysis. Application of a conventional single-channel AA (atomic absorption) device to air monitoring would, therefore, limit monitoring to a single element at a time. Single-channel AA spectrometry is achieved with low cost medium-resolution monochrometers by using narrow, single-element, line sources (e.g., hollow-cathode lamps). However, a variety of multi-element instruments have been designed using continuum source technology, for example, a 16-channel instrument, termed SIMAAC (for simultaneous multi-element atomic absorption with continuum source). Based on a continuum source and echelle polychrometer, the SIMAAC was capable of measuring up to 16 elements, simultaneously, with either flame or graphite-furnace atomization. Absolute multi-element detection limits achieved with standard solutions were a few pg for Cu, Cr, Mg, Mn, and Zn; about 15 pg for Co; and in the 50 pg range for Fe and V. These compared favorably with conventional, single-element AA; and were uniformly better than those achieved by inductively-coupled plasma-Atomic Emission Spectroscopy (ICP-AES).

The basis of the SIMAAC instrument was a high-resolution, Spectraspan III Eschelle polychrometer which resolves incident light into component wavelengths onto a two-dimensional spatial array at the exit plane where 20 exit slits were located on a removable mask or "cassette". Because of their large size, pinhead mirrors mounted within the cassette are needed to direct the light from the slits to a fixed array of 20 photomultiplier tubes.

Both Hitachi and Thermo Jarrell Ash (TJA) have built instruments capable of simultaneous analysis of 4 elements using hollow-cathode lamps. The former was originally designed in the late 1980s and employs four-photomultiplier tubes to allow simultaneous monitoring of each element. The latter is a single-channel scanning instrument and has been successfully used the TJA instrument to simultaneously analyze Cd and Pb in blood with graphite furnace atomization.

Perkin Elmer (PE) has recently introduced an element GFAAS, referred to as the SIMAA 6000. The instrument uses a specially-designed, high-dispersion, high-luminosity, Tetrahedral Echelle Polychrometer and a monolithic detector incorporating high-performance, UV-optimized, photodiodes. The detector is located at the focal plane of the polychrometer and individual photodiodes are positioned at the primary resonance lines of each of 38 elements and at the secondary lines of a number of key elements. Data collection is achieved with eight independent analog channels using eight separate analog-to-digital converters. A maximum of 6 elements can be determined simultaneously with PE's software. Elements measurable in multi-element mode include: Be, Mg, Ca, Sr, Ba, Ti, V, Cr, Mo, Mn, Fe, Co, Ni, Cu, Zn, Mo, Ru, Ag, Cd, Au, Hg, B, Al, Si, P, Ge, As, Se, In, Sn, Sb, Te, Ti, and Pb. The instrument comes with PE's transversely-heated graphite analyzer (THGA) which may provide a uniform temperature profile across the length of the furnace tube. This feature reduces memory effects experienced with older designs which employ constant heating only at the center.

Memory effects in the latter are exacerbated by condensation of analytes in cooler regions at the ends of the tube. The furnace tube is designed with an integral L'vov platform to allow more rapid sample heating, which permits atomization of refractory elements (e.g., V, Ti, and Mo) from the L'vov platform and lower optimum atomization temperatures. Perkin Elmer also incorporates a longitudinal Zeeman-effect background corrector which eliminates the need for polarizers in the optical system. Zeeman background correction is generally effective in correcting for apparent background absorption caused by scatter from droplets and smoke particles. As discussed above, this is important for direct solids analysis. Despite the extra optics required to combine light sources, high polychrometer luminosity and detector sensitivity afford detection limits that are, in fact, marginally better than those achieved by earlier single-element instruments.

While various studies demonstrate the efficacy of direct particulate analysis, the development of a true near-real-time instrument is precluded by the low sampling rates (i.e., 1 to 10 L/min) achieved by direct impaction and filtration schemes employed for sample collection. Most of the elements could be routinely detected, even at the lowest concentrations observed in ambient air, only if the sample volume was increased to 2 m³. Delivery of aerosol particulate matter associated with this much air may be achieved in 10 minutes if an effective flow rate of 200 L/min flow rate could be accommodated by direct impaction into a graphite furnace platform. This would be highly desirable in the aerosol chemical analysis.

Aerosol concentration is described in aerosol exposure studies (Sioutas, C., Koutrakis P., and Olson, B. A., "Development of a low cutpoint virtual impactor," *Aerosol Science & Technology* 21:223–236, 1994; Sioutas, C., Koutrakis, P., and Burton, R. M., "Development of a low cutpoint slit virtual impactor for sampling ambient fine particles," *Journal of Aerosol Science*, 25: 1321–1330, 1994b; Sioutas, C., Koutrakis, P., and Burton, R. M.; "A high volume small cutpoint virtual impactor for separation of atmospheric particulate from gaseous pollutants," Particulate *Science and Technology*, 12:207–221, 1994c; and, Sioutas, C., Koutrakis, P., Ferguson, S. T. and Burton, R. M.; "Development and evaluation of an ambient particles concentrator for inhalation exposure studies," *Inhalation Toxicology*, 7(5):633–644 1995). The aerosol concentration device is essentially a virtual impactor capable of achieving a cutpoint of approximately 0.1 μm for aerosol particles.

The physical principle of operation of a virtual impactor is similar to that of an inertial impactor, as both methods use particle inertia to separate particles from gases. A jet of particle-laden air is deflected abruptly by an impaction plate which causes an abrupt deflection of the air streamlines. Particles larger than a critical size (the so-called cutpoint of the impactor) cross the air streamlines and, in the case of an inertial impactor, are collected on the impaction plate, while particles smaller than the critical size follow the deflected streamlines. The main difference between an inertial and a virtual impactor is that in the latter, particles are directed into a collection nozzle rather than onto a collection plate. To separate larger particles continuously from the collection probe, a fraction of the total flow, referred to as the minor flow (typically 10%–20% of the total flow), is allowed to pass through the probe, leaving particles larger than the cutpoint contained in a small fraction of the gas. Particles larger than the cutpoint are, therefore, concentrated into the minor flow, nominally by a factor of the inverse of the minor flow ratio (i.e., particles are concentrated 20-fold for a minor flow of 5 L·min⁻¹ and total flow of 100 L·min⁻¹).

The cutpoint of an impactor is determined by several parameters through the Stokes number.

$$St = \frac{\rho_p d_p^2 U C_c}{9\eta D_j} \quad (1)$$

where $\rho_P$ is the particle density, $d_P$ is the particle diameter, U is the impactor jet velocity, $\eta$ is the gas viscosity, and $D_j$ is the diameter of the impactor jet (Hinds, "Aerosol Technology", 1982, John Wiley & Sons, Inc.). The slip correction factor, $C_c$, corrects for the reduced drag on small particles as they approach the mean free path of the gas. The collection efficiency for an impactor is often characterized by its D50, the diameter at which 50% of the input particles are collected. To collect particles as small as 0.05 μm by impaction, a very high pressure drop is required.

The slip correction factor is given by the following equation:

$$C_c = 1 + \frac{2}{Pd_p}[6.32 + 2.01\exp(-0.1095 Pd_p)] \quad (2)$$

where P is the absolute pressure in Cm Hg and $d_P$ is the particle diameter in μm.

Virtually all of the mass of the various elemental constituents of the atmospheric aerosol lie in or above the aerosol accumulation region, i.e., at diameters >50 nm. Therefore, a sampler designed to collect all of this material would need a cutpoint in this range. However, as predicted by equation (1), for such a small particle size to be collected, velocities greater than 150 m/s and nozzle sizes smaller than 0.04 cm are required. Nozzles smaller than 0.03 cm are difficult to manufacture by conventional means and may result in excessive particle losses due to particle impaction onto the lateral nozzle walls. This sets an upper limit to the sampling flow of the aerosol entering the virtual impactor and, even when the velocity of the aerosol equals the speed of sound (approximately 300 m/s at standard temperature and pressure), the total flow rate will be on the order of 1 L/min. Use of nozzles producing such high flow rates produces a very high pressure drop (>75 kPa) (Marple, V. A. and Willeke, K. (1976) Impactor Design. *Atmos. Environ.*, 10, 891–896.) This requires a large pump and presents problems of preventing clogging of the impactor jets by larger particles if sufficient particulate mass is to be collected in periods ≦1 hour. Additionally, operation of the impactor at sonic or compressible flow conditions has been shown to result in reduced pressure and temperature at the impactor's jet, thus distorting the physicochemical properties of the sampled aerosol. Loss of volatile compounds may lead to particle shrinkage. Also, aerodynamic cooling associated with the adiabatic expansion of the high-speed jet may cause particle growth.

Multi-orifice impactors have been proposed as a potential sampling method to overcome the problem low flow rate (Marple et al., "High-volume impactor for sampling fine and coarse particles", *J. Air Waste Manag. Assoc.*, 40: 762–767, 1990). However, fluid dynamic interactions between the micro-orifice jets have been shown to decrease the impactor's collection efficiency, in some cases to values below 50%. Still further, constructing a virtual micro-orifice impactor requires the construction of an equally large number of collection nozzles. Potential misalignments between the acceleration and collection nozzles, along with the aforementioned jet interactions, may substantially increase the internal particle losses, which are a typical shortcoming of single-nozzle virtual impactors. Particle losses as high as 80% have been observed (Chen et al., "Performance of a Modified Virtual Impactor", *Aerosol Sci. & Technology*, 5:369–376, 1986) or predicted for some single-nozzle virtual impactors.

In virtual impactors, most of the loss occurs for particles with diameters nearly equal to the cutpoint. Thus, much higher concentration factors can be achieved without large losses if the cutpoint were much less than the smallest particle size to be separated. This is clearly limited by pressure drop to the 0.1 $\mu$m region.

Despite some of the advantages of current techniques for aerosol particles analysis, it is clear that the current technology is insufficient to achieve convenient sample delivery for multi-element analysis at sub-hourly intervals due to lack of adequate sample amount which current technology is capable of collecting during a short period of sampling time. Therefore, an aerosol particle sampling technique which permits collection of sufficient material in less than 30 minutes for near real-time on-line (or off-line) multi-element analysis is needed in the art.

SUMMARY OF THE INVENTION

It is an object of the present invention to provide a method and system for sampling aerosol particles in sufficient quantities for near-real time on-line or off-line analysis using short sampling periods.

It is another object of the present invention to provide a system and method for aerosol particle multi-element chemical analysis with high collection efficiency, wherein air is sampled at a flow rate of not less than 170 L/min, and particles are grown by condensation of water vapor in a condenser after aerosol saturation by direct injection of steam, where the resulting droplets are concentrated using a multi-nozzle virtual impactor and collected in liquid slurry with a real impactor either for direct injection into a multi-element graphite furnace atomic absorption apparatus for near-real time on-line chemical analysis of the ambient aerosol, or for filling sample vials for subsequent off-line analysis. According to the teachings of the present invention, a system for multi-element chemical analysis of aerosol particles includes:

a particle concentrator unit for receiving initial particle-laden flow of ambient air and discharging a concentrated air flow containing droplets obtained by condensational growth of the initial particles, a real impactor for receiving the concentrated air flow from the particle concentrator unit and discharging liquid slurry containing enlarged droplets therefrom, and a device for multi-element analysis of the slurry received from the inertial or real impactor (for example, Graphite Furnace Atomic Absorption Analyzer).

The diameter of the droplets is in the range of 0.7–12 $\mu$m.

The liquid slurry may either be delivered into a series of sample vials for an off-line analysis by the device for multi-element analysis or may be delivered thereto directly for on-line analysis.

The particle concentrator unit includes:

a saturator receiving the initial particle-laden flow of ambient air and a flow of steam and discharging a saturated aerosol laden with the initial fine particles, a condenser coupled to the saturator for receiving the saturated aerosol and condensationally growing the initial fine particles in diameter thereof to produce droplets of the enlarged diameter, and a virtual impactor coupled to the condenser for receiving the air flow laden with the large droplets and for separating the droplets exceeding the predetermined diameter, to obtain the concentrated air flow containing said droplets.

Preferably, the initial particle-laden flow of ambient air is supplied to the saturator at the flow rate in the range 170–260 L/min.

A controllable heater is coupled to the saturator to heat it to a predetermined temperature, while cooling means is coupled to the condenser for maintaining the walls at a predetermined temperature (0.5° C.–10° C.).

The flow rate of the air laden with droplets is received at the virtual impactor at a flow rate of approximately 200 L/min, while the concentrated minor air flow laden with droplets is expelled from the virtual impactor at 10 L/min.

Additionally, the present invention is a method of multi-element analysis of aerosol particles, which includes the steps of:

supplying a flow of ambient air laden with initial particles to a saturator, injecting a flow of steam to said saturator for mixing with the ambient air and for saturating it, directing the saturated ambient air from the saturator into a condenser for condensational growth of the initial particles to produce an air flow laden with droplets of a diameter larger than diameters of the initial particles, supplying the air flow laden with said droplets to a virtual impactor, for separating from an overall air flow, a concentrated air flow containing the droplets exceeding a predetermined diameter, and then directing the concentrated air flow from the virtual impactor to a real or inertial impactor for forming a liquid slurry containing droplets exceeding the predetermined diameter, and exposing said liquid slurry to a multi-element analysis.

DESCRIPTION OF THE PREFERRED EMBODIMENTS

Figure 1:
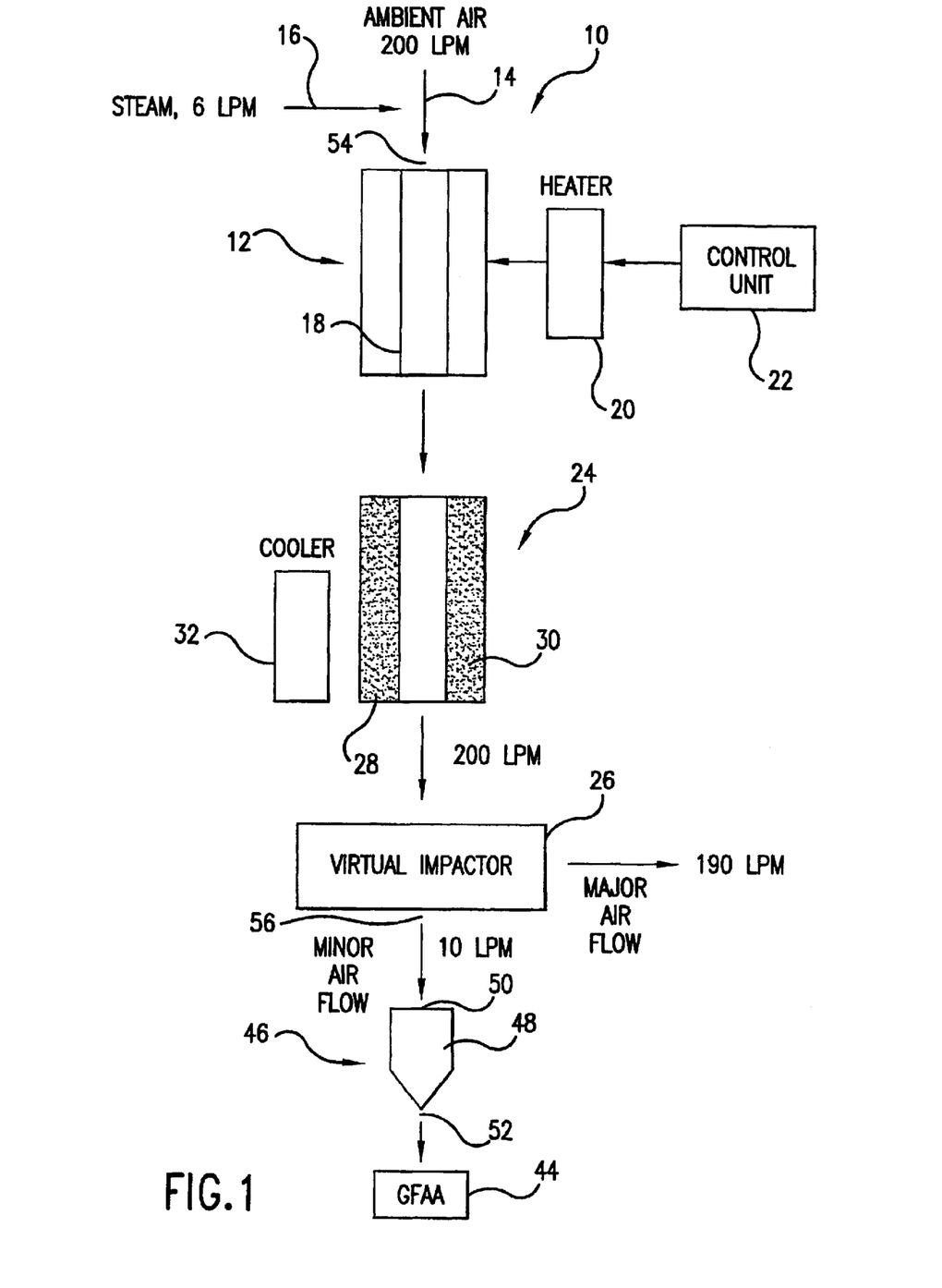
FIG. 1 is a schematic diagram of aerosol concentrator system of the present invention.

Referring to FIG. 1, a sample collection system 10 includes a saturator 12 into which an aerosol 14 (the ambient air) is first drawn at a sampling flow rate of 200 L/min and mixed with steam 16 injected radially through a porous walled tube 18 of the saturator 12 to achieve saturation of the aerosol. An ambient temperature and the steam flow rate of 6 L/min (or less) is generally adequate to saturate the aerosol. To insure mixing of the ambient air and the steam, the aerosol/steam mixture is delivered to a saturator chamber which consists of a tube 18 approximately 29 cm long and 2.7 cm in diameter to provide a residence time of about 1 ms which should guarantee saturation of the sampled air. The tube 18 is kept at a temperature of 35° C. with a heater 20 controlled by a control circuit 22.

Subsequently, the saturated air from the saturator 12 is drawn through a pair of condensers 24 that allow the fine particles delivered into the saturator to grow to a diameter in the range of 0.7–10 μm. The sub-system including the saturator 12 and the condenser 24 grows the particles by condensing water on them (thus, creating large droplets).

The condensers 24 consist of two coaxial glass tubes 28, 30, having approximate dimensions 97 cm in length and diameters of 3.4 cm. and incorporate an exit chamber configured to remove excess water lost to the walls. The design and dimensions are directed to a system which provides for a residence time in the condensers 24 of about 0.6 seconds for a flow of 200 L/min. across the condenser 24 and maximize the efficiency of the supersaturation process. The condenser 28, 30 are maintained at temperature 0.5° C. with a refrigerant cooler 32.

The particle growth through the vapor condensation is the basic principle used in the saturator/condenser sub-system. The degree of supersaturation required depends on particle size which for hydrophobic particles <0.1 μm in diameter, is given by the Kelvin equation:

$$Supersaturation = \frac{P}{P_s} = \exp\left(\frac{4\sigma M}{\rho R T d_p}\right) \quad (3)$$

where p is the actual vapor pressure;

$p_S$ is the saturation vapor pressure at a given temperature;

M, ρ and σ are the molecular weight, density, and surface tension of the condensing liquid;

R is the gas constant; and $d_P$ is the critical particle diameter, also called Kelvin diameter. The Kelvin diameter defines the critical equilibrium diameter at which a pure droplet is stable at the critical saturation ratio needed for equilibrium. At the critical saturation ratio, particles larger than the critical diameter will grow by condensation, while smaller particles will evaporate. Conversely, smaller critical diameters will be achieved by applying higher saturation ratios, i.e., resulting in particle growth by condensation, while at lower saturation ratios, the particle will evaporate.

Equation 3 is only valid for a pure liquid surface. When dissolved salts (e.g. ammonium sulfate and nitrate in atmospheric aerosols) are present, the equilibrium vapor pressure above the droplet surface is reduced. This reduces the required saturation ratio for condensational growth to occur compared to a pure liquid. Adding the correction for a dissolved salt, and after particles have grown substantially, Equation 2 now becomes (Hinds, W. C. Aerosol Technology: Properties, Behavior, and Measurement of Airborne Particles, 1982, John Wiley & Sons, New York.)

$$S = \frac{P}{P_s} = \left(1 + \frac{6imM_v}{M_s\rho\pi d^3}\right)^{-1} \exp\left(\frac{4\gamma M_v}{\rho R T d}\right) \quad (3)$$

where m and $M_S$ are the mass and molecular weight of the salt, and i is the number of ions per salt molecule.

A supersaturation of 1.24 is required to condense water on 0.01 μm particles. The ultimate size to which particles grow depends on the time of exposure to the saturated vapor. As the dynamics of condensation dictate that small particles grow rapidly and large particles grow slowly, the resulting size distribution becomes quite nearly unimodal. It is possible to grow particles, in a near uniform manner to a size of 12 μm.

Enlarged particles (i.e., now droplets) of this size may be easily separated at a low pressure drop with the virtual impactor 26 having a cutpoint of 0.7 μm (aerodynamic particle diameter). As the particles tend to are grow to a uniform size, losses in the device tend to be independent of the original size.

The target supersaturation ratio to be achieved is on the order of 3.0 to insure activation of all particles. The choice of parameters such as the temperature of the saturator 12 and condenser 24 is generally determined empirically. From the Kelvin equation (3), supersaturation 10 is adequate for activating a water droplet as small as 0.003 μm (M=18 g/mole, σ=72 dyn/cm, ρ=1 g/cm³). Nevertheless, a supersaturation value as high as 300% may be chosen to account for excess moisture is required to account for condensation of water vapor occurring onto the cold walls of the condenser and the complexity of condensational growth for real polydisperse, multimodal, multicomponent aerosol.

For droplets smaller than the mean free path of the gas (about 0.066 μm for air), the rate of growth in this region is determined by random molecular collisions, given by the kinetic theory of gases as (Hinds, W. C. (1982) Aerosol Technology: Properties, Behavior, and Measurement of Airborne Particles, John Wiley & Sons, New York.)

$$\frac{dd_p}{dt} = \frac{2M_v(P_\infty - P_d)}{\rho_p N_a \sqrt{2\pi m_v kT}} \quad (4)$$

where $P_d$ is the vapor pressure at the droplet surface, given by the Equation 3, $P_{oo}$ is the vapor pressure away from the droplet, $N_\alpha$ is Avagadro's number, $m_v$ is the mass of a vapor molecule, and k is Boltzmann's constant. The growth rate for particles smaller than the mean free path of the gas is, therefore, independent of the particle size. For particles larger than the mean free path of the gas, the rate of growth is governed by the rate of diffusion of vapor to the particle surface given by (Hinds, W. C. (1982) Aerosol Technology: Properties, Behavior, and Measurement of Airborne Particles, John Wiley & Sons, New York.)

$$\frac{dd_p}{dt} = \frac{4D_v M_v}{R\rho_p d_p}\left(\frac{P_\infty}{T_\infty} - \frac{P_d}{T_d}\right) \quad (5)$$

where $D_v$ is the diffusion coefficient for the condensing vapor. Thus, the growth rate for particles larger than the mean free path of the gas is inversely proportional to the particle size. This will cause all particles larger than the Kelvin diameter to approach an equilibrium size, determined by the time and amount of vapor available for condensation.

The two equations for growth can be combined into a single expression by applying the Fuchs and Sutugin (Fuchs, N. A. and Sutugin, A. G. (1970) Highly Dispersed Aerosols, Ann Arbor Science Publishers, Ann Arbor, Mich.) correction factor, $f(Kn)$, to Equation 5

$$\frac{dd_p}{dt} = \frac{4D_v M_v}{R\rho_p d_p}\left(\frac{P_\infty}{T_\infty} - \frac{P_d}{T_d}\right) f(\lambda, d_p) \quad (6)$$

$$f(\lambda, d_p) = \frac{d_p + 2\lambda}{d_p + 3.42\lambda + 5.33\left(\frac{\lambda^2}{d_p}\right)} \quad (7)$$

where λ is the mean free path of the vapor or gas molecules. Since vapor is condensing onto the droplet surface, an additional correction must be applied to account for heating 
of the droplet due to the latent heat of condensation and the heat lost by conduction to the cooler surrounding air. The resulting temperature correction is given by (Ahn, K.-H. and Liu, B. Y. H. (1990) Particle Activation and Droplet Growth Processes in Condensation Nucleus Counter-I. Background. J. Aerosol Sci., 21, 249–261.)

$$T_d - T_\infty = \frac{D_v M_v H}{Rk_v}\left(\frac{P_d}{T_d} - \frac{P_\infty}{T_\infty}\right)\frac{f(\lambda_v, d_p)}{f(\lambda_g, d_p)} \qquad (8)$$

where H is the latent heat of condensation, and $k_v$ is the thermal conductivity of the condensing vapor.

To determine the time required for condensational growth, Equations 6–8 must be solved iteratively and integrated over the initial to final particle sizes. During growth, the saturation ratio will be decreasing due to loss of vapor by condensation to the walls of the condenser as well as to the particles. To a lesser extent, the saturation ratio will also be lowered due to the effects of latent heat production on the particles. These factors make theoretical growth rate calculations suitable only as a guideline for experimental characterization.

For growth to occur on particles as small as 0.01 $\mu$m in diameter, Equation 2 predicts a critical saturation ratio of 1.24. The maximum time required for condensational growth may then be estimated by assuming a saturation ratio of 1.25. Since dissolved salts will only serve to aid condensational growth, the particles are assumed to be insoluble and Equation 3 may, therefore, be ignored. From Equation 4, approximately 0.1 ms is needed for particles to grow from 0.01 $\mu$m to 0.1 $\mu$m in diameter, when growth by diffusion of water vapor becomes dominant. Equation 5 predicts an additional 30 ms is required for growth from 0.1 $\mu$m to 5 $\mu$m diameter. After applying the correction factors in Equations 6–8, the estimated time for particle growth from 0.01 $\mu$m to 5 $\mu$m in diameter is 33 ms, i.e., much less than the residence time of aerosol in the condensors.

Figure 3:
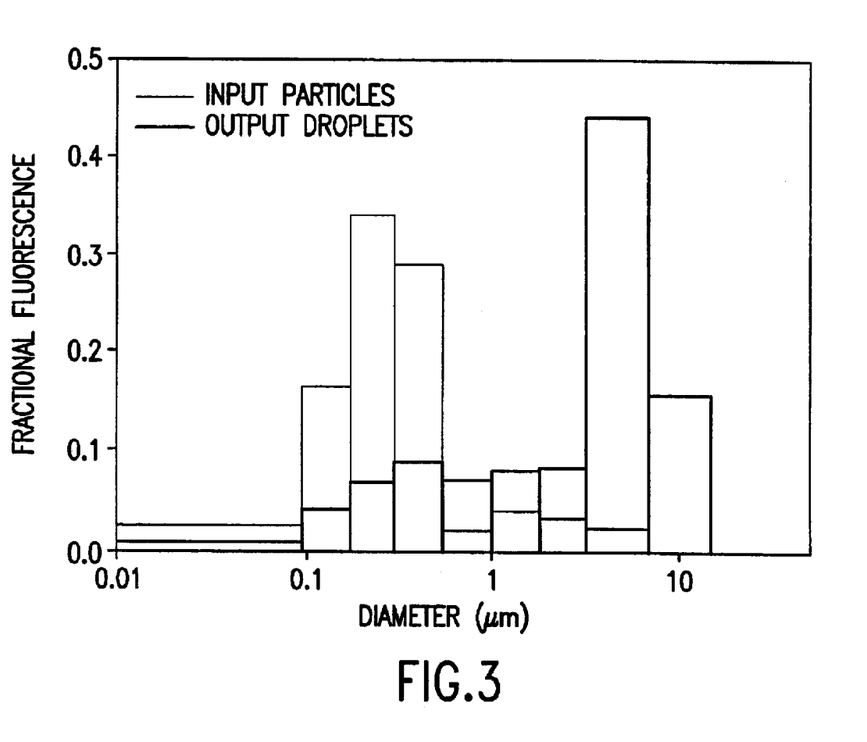
FIG. 3 is a diagram showing size distribution for 0.084 $\mu$m particles before and after condensational growth.

After passing through the condenser 24, the aerosol is drawn through a virtual impactor 26 with a 0.7 $\mu$m cutpoint. The physical principle of operation of a virtual impactor is similar to that of an inertial impactor, as both methods use particle inertia to separate particles from gases. A jet of particle-laden air is deflected abruptly by an impaction plate, which causes an abrupt deflection of the air streamlines. Particles larger than a critical size (the so-called cutpoint of the impactor) cross the air streamlines and, in the case of an inertial 
fluorescence vs. particle size spectra for 0.084 µm particles before and after condensational growth. The relatively high concentration for 0.084 µm particles results in multiple particles becoming entrained in each nebulizer droplet, which increases the mean dry particle diameter to about 0.3 µm. This agglomeration effect is greatly reduced for 0.209 µm diameter particles and negligible for larger particles. Following condensational growth, the mean size of the grown droplets increases to about 4 μm, with 65% of the droplets >3 μm in diameter. The efficiencies for the virtual and real impactors were measured using dry PSL particles with no condensational growth. The transmission efficiency versus particle size curve for the virtual impactor (FIG. 5) for dry particles ranging in size from 0.1 to 6 μm indicates a 50% cutpoint of about 1.8 μm in diameter. This corresponds to a Stokes number of 1.4.

The entire system is made from glass, Teflon, and nylon, to prevent contamination of the collected slurry samples. The system is mounted vertically to prevent losses by particle sedimentation.

The aerosol concentrator system 10 can be mated with a Perkin Elmer SIMAA 6000 graphite furnace instrument 44. As a compromise between high temporal resolution and collection of adequate sample, target sampling times of about 10 min were investigated. Analysis times for solid materials were typically of the order of 30 s for ashing and 3 or 4 seconds for atomization. One or two additional firings may be required to clean out the graphite furnace. Thus, the sample throughput rate is expected to be controlled by the sampling time rather than by the analysis time. The principles of the GFAA based multi-element analysis is well known to those skilled in the art, and therefore, are not intended to be discussed herein in detail.

In the system of the present invention, particles (e.g., droplets) associated with the 10 L/min aerosol flow from the concentrator can be delivered directly into the furnace 44 with a single, circular jet, real or inertial impactor 46, as best shown in FIG. 2. The largest impactor jet diameter which can be inserted into the graphite furnace port is 1.5 mm. At a flow rate of 10 L/min, it is calculated that the cutpoint of the impactor 46 is about 0.7 μm, i.e., far smaller than needed to collect the supermicrometer-size droplets emerging from the concentrator.

The impactor 46 (best shown in FIG. 1) consists of a body 48 with internal diameter smoothly tapering from about 9 mm at the inlet 50 to 1 mm at the outlet 52 over a distance of the order of about 10 cm. Both the virtual impactor 26 and the impactor 46 can be machined from high-purity aluminum. The impactor nozzle is machined from high-purity tantalum or like material.

Assuming an initial aerosol concentration at the inlet 54 of the concentrator system 10 of 50 μg $m^{-3}$, initial particle size of 0.5 μm, and final droplet size of 10 μm, then about 200 μL of water associated with the droplets enter the graphite furnace 48 during a 10-minute sampling period. Only about 3 mL of water is associated with the droplets if all of the original aerosol mass were contained in 0.2-μm particles. Either of these amounts of water can easily be controlled by changing the condenser temperature and by heating the furnace during collection. The impaction probe may be heated slightly to prevent condensation of the 2 mL of water vapor associated with the (saturated) 100 L of air (i.e., 10 L/min for 10 min) sampled during this period.

To aspirate the aerosol into the graphite furnace 44, optical-quality quartz end caps are installed to seal the furnace 44. This can be accomplished without substantial reduction in beam intensity. The pressure drop required by the impactor 46 is about 0.05 Atm (i.e., 5 cm of Hg) and is achieved by withdrawing air from a port in the edge of the quartz endcaps with a small leak-free diaphragm pump. The flow rate is monitored with a precision flow meter mounted at the exit of the pump.

With large droplets, the impactor nozzle 52 does not need to be inserted much past the wall of the furnace tube, although, optimum positioning is established experimentally, by aspirating fluorescent monodisperse test particles of the proper size and measuring the collection efficiency using the method described in above paragraphs. It is envisioned that an adequate seal can be achieved (although none may be needed) between the impaction probe and the graphite furnace port by friction. The impaction probe may be attached to a mechanical retractor to remove it before firing the furnace 44. This will permit additions of standards and matrix modifiers using the systems auto sampler and will prevent clogging and damage to the impaction probe. A switching valve 98 is used to divert the sample flow during analysis periods. The retracting impactor nozzle can be plumbed to the concentrator outlet 56 with a piece of flexible tubing using Teflon or like material, such that the length of tubing is straight and vertical during sampling.

The concentrations of respirable aerosol particles typically varies between 20 and about 50 μg $m^{-3}$. At the target sampling rate and time (200 L/min for 10 min), the total aerosol mass delivered to the furnace 44 at the higher concentration is only 100 μg, i.e., an amount well below the 1 or 2 mg introduced in slurry analyses described above. Under these conditions, memory effects (associated with heating regimes of the furnace 44) of the GFAA are likely to be less of a problem than experienced in other solids analyses. Clearly, larger mass loadings might be tolerated, provided they are delivered by the concentrator system 10 of the present invention. Should memory effects be important, experimentation with matrix modifiers, e.g., chlorides, which may be introduced into the furnace 44 with the autosampler and fired between analyses can be accomplished.

The conditions of the graphite furnace 44 are dictated by the elements to be analyzed. The atomization temperature must be high enough so that even the least volatile element is atomized, however ashing temperature must be low enough that most of the volatile elements are not volatilized prior to analysis. Recommended furnace conditions for individual analysis of a wide range of elements are shown in Table 1. The data suggest that Ag, Cd, Pb, and Zn may be determined simultaneously, or similarly, As, Sb, Se, and Mn; and Al, Co, Cr, Cu, Fe, Ni, and S. However, Fe, for example, is so abundant in aerosol particles that the determination may be made at conditions far from the optimum. The choice of elements that can be determined simultaneously depends on the atmosphere to be sampled.

Instrument calibration for solid sample analyses has been done by running standard solutions, in this case, multielement standards; and with standard addition techniques in which the sample is spiked with a known amount of the element(s) to be determined.

TABLE 1

Ashing and Atomization temperatures for Various Elements Determinable by GFAA.

| | Recommended Temperatures (1), C. | | Compromise Temperatures, C. | |
|---|---|---|---|---|
| Element | Ashing | Atomization | Ashing | Atomization |
| Ag | 1000 | 1800 | 900 | 1700 |
| Cd | 900 | 1600 | | |
| Pb | 850 | 1800 | | |
| Zn | 700 | 1800 | | |

TABLE 1-continued Ashing and Atomization temperatures for Various Elements Determinable by GFAA.

| Element | Recommended Temperatures (1), C. | | Compromise Temperatures, C. | |
|---|---|---|---|---|
| | Ashing | Atomization | Ashing | Atomization |
| As | 1300 | 2100 | 1200 | 2100 |
| Sb | 1100 | 2000 | | |
| Se | 1100 | 2100 | | |
| Mn | 1400 | 2200 | | |
| Al | 1700 | 2500 | 1400 | 2400 |
| Co | 1400 | 2500 | | |
| Cr | 1650 | 2500 | | |
| Cu | 1300 | 2500 | | |
| Fe | 1400 | 2400 | | |
| Ni | 1400 | 2500 | | |
| Sn | 1400 | 2300 | | |

Figure 2:
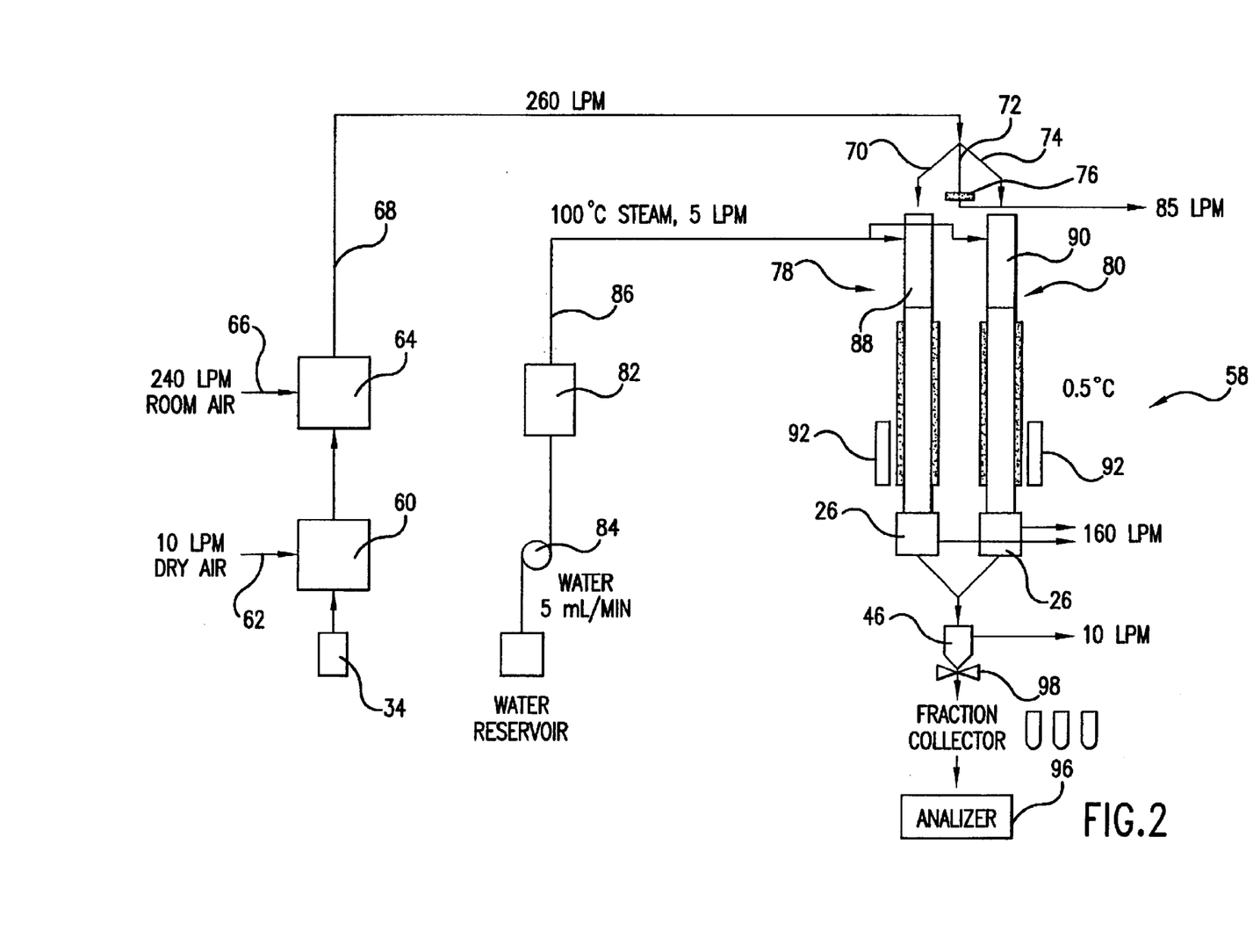
FIG. 2 is a schematic diagram of the testing set-up for the overall system for chemical analysis of the aerosol particles of the present invention.

Referring to FIG. 2, the set-up for testing of the overall system 58 is schematically presented. Test aerosol is generated by nebulizing a suspension of monodisperse florescent polystyrene latex (PSL) particles (Polysciences, Inc., Warrington, Pa.) with the commercial nebulizer 34 (Micro-Mist Model 4650D, Devilbis, Somerset, Pa.). Suspensions of 0.084, 0.209, 0.495, 0.930, 1.881, 2.977, and 5.895 μm diameter PSL are prepared by diluting a 50 μL aliquot of each stock solution to 100 mL with 18.2 MΩ water. Hydrophobic PSL particles are known to be grown by condensational growth to the same extent as hygroscopic atmospheric aerosol particles such as ammonium sulfate and potassium nitrate.

The aerosol is initially mixed in a chamber 60 to form dry test particles, then mixed in the mixing chamber 64 with room air 66 to make up the total flow 68 prior to entering the saturator/condenser/virtual impactor system 10. The airflow 68 is split into 3 equal flows 70, 72, 74 of 85 L/min for the reference filter 76 and two condensational growth columns 78, 80. The reference filter 76 is a 47-mm diameter Teflon filter (Teflo, 2 μm pore, Gelman Laboratory, Ann Arbor, Mich.) which provides a measure of the particle concentration prior to entering the system 10.

Steam is generated by steam generator 82 by delivering 18.2 MΩ water with a multichannel peristaltic pump 84 (Minipuls 3, Gilson, Inc., Middleton, Wis.) to heated flasks. The steam 86 is then injected coaxially into the airstream through a coarse-fritted glass collar in each steam injector 88, 90, which represents a cylindrical glass tube 27 mm in diameter and 450 mm in length.

Turbulence within the steam injector 88, 90 causes rapid mixing of the steam 86 and air which becomes saturated at approximately 35° C. The saturated air then enters the condensers 24, which include cylindrical glass tubes approximately 33 mm in diameter and 970 mm in length, which are maintained at 0.5° C. by a recirculating chiller 92 (Polystat Model 12910-10, Cole-Parmer Instrument Co., Vernon Hills, Ill.). A water trap built into the bottom of each condenser collects and removes water that condenses on the walls. Within the condensers 24, the air is rapidly cooled to about 25° C., giving a maximum theoretical saturation ratio of 1.8. Vapor loss due to condensation on the walls of the condenser and onto the particles reduces the actual saturation ratio to some extent. A saturation ratio of only 1.25 is needed to grow hydrophobic particles as small as 0.01 μm by condensational growth.

The grown particles in the form of droplets, are concentrated using a 2-nozzle glass virtual impactor 26 operating at a major flow of 160 L/min and a minor flow of 10 L/min. The 3 mm diameter acceleration nozzle and 4.5 mm diameter collection nozzle produce a 50% cutpoint of approximately 2 μm at a pressure drop of 24 kPa. A glass single-jet real impactor 46 with a 1.9 mm diameter jet and 50% cutpoint of 1 μm is used to separate the concentrated droplets from the airflow. The droplets accumulate in the bottom of the real impactor 46 in a liquid slurry at about 0.2 mL/min. Following a 30 minute collection period, the slurry is hydraulically delivered to an X-Y fraction collector 94 (Foxy, Isco, Lincoln, Nebr.) and stored in glass sample vials for subsequent analysis. It is also possible and is contemplated in the scope of the present invention, to deliver the liquid slurry directly into the graphite furnace 44 for on-line analysis.

Extensive control and automation of the collection process of the present invention is accomplished using a computer-controller datalogger (Model CR23X, Campbell Scientific, Inc., Logan, Utah). Volumetric air flow rates are precisely maintained using control valves and mass flow meters corrected to ambient temperature and pressure. The steam injection rate is determined by the datalogger based on ambient temperature and relative humidity and the desired saturation ratio, with the peristaltic pump speed automatically updated every 10 s. At the end of a sample collection period, ball valves are closed to isolate the real impactor 46, which is then pressurized using compressed air to expel the accumulated slurry. The fraction collector 94 automatically advances to the next sample collection vial after the slurry is dispensed, and the next sample collection begins.

Following efficiency tests made with fluorescent particles, the liquid samples were vacuum dried overnight at room temperature. The fluorescein dye on the reference filters 76 and dried samples may be extracted with 10 mL aliquots of ethyl acetate. To determine losses within individual components of the system, each component was washed with ethyl acetate and 2-propanol, with the washes collected, dried, and dissolved with 10 mL ethyl acetate. The fluorescence intensity of each sample may be determined with a spectrofluorophotometer (Model RF-5301PC, Shimadzu Corporation, Columbia, Md.) using an excitation wavelength of 440 nm and integrating the emission intensity from 450 to 600 nm. The collection efficiency is calculated as $$\mathit{Eff} = \frac{F_S/O_S}{F_R/O_R} \tag{6}$$

where F is the integrated fluorescence intensity,
O is the flow rate, and
the subscripts S and R refer to the sample and reference, respectively.

To determine the system blank for various potential analytes, an absolute fluted filter capsule (3-μm pore Model 12116, Gelman Laboratory, Ann Arbor, Mich.) may be installed at the sampler inlet and the system operated for two 30-minute periods and the resulting aqueous samples acidified to achieve a 0.5% concentration of nitric acid and analyzed by direct injection into a multi-element GFAAS 96 with Zeeman background correction (SIMAA 6000, Perkin Elmer Corp., Danbury, Conn.) for Al, As, Cd, Cr, Cu, Fe, Mn, Ni, Pb, Sb, Se, Zn.

The size distributions for the rest PSL particles are measured before and after condensational growth using a micro-orifice impactor to segregate the aerosol into 9 size ranges from 0.01 to 15 μm. The particle concentrations are kept as low as practical to reduce agglomeration, while still being detectable in a 30 minute sample, but the effects are still evident for particles <0.5 μm.

FIG. 3 shows fluorescence vs. particle size spectra for 0.084 μm particles before and after condensational growth. The relatively high concentration for 0.084 μm particles results in multiple particles becoming entrained in each nebulizer droplet, which increases the mean dry particle diameter to about 0.3 μm. This agglomeration effect is greatly reduced for 0.209 μm particles and negligible for larger particles. Following condensational growth, the mean size increases to about 4 μm, with 65% of the droplets >3 μm.

Figure 4:
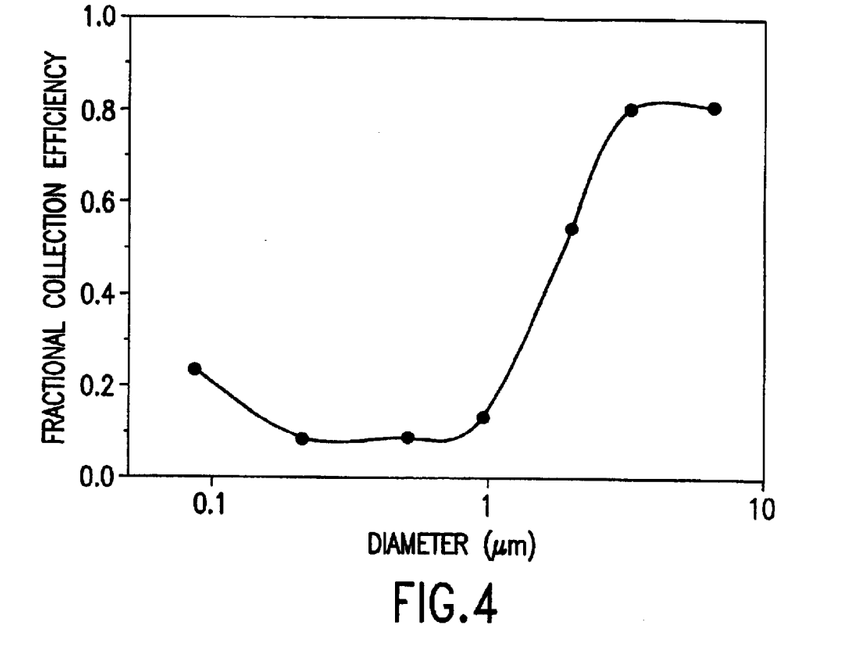
FIG. 4 is a diagram showing collection efficiency vs. size of the particles for the virtual impactor.
Figure 5:
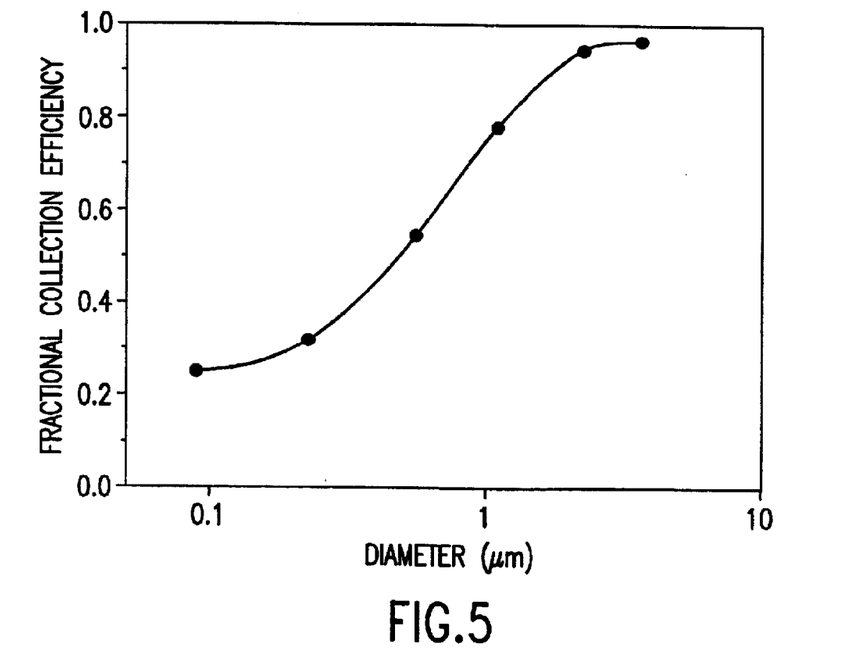
FIG. 5 is a diagram showing collection efficiency vs. particles size for an inertial or real impactor.

The collection efficiencies for the virtual and real or inertial impactors were measured using dry PSL particles with no condensational growth. The collection efficiency vs. particle size curve for the virtual impactor (shown in FIG. 4) for dry particles ranging in size from 0.1 to 6 μm indicates a 50% cutpoint of about 1.8 μm. For particles 3 μm and larger, the collection efficiency is 80%, which results in a concentration factor of 13.6 for large particles in the minor flow. The collection efficiency curve for the real impactor for dry particles ranging in size from 0.1 to 3 μm, shown in FIG. 5, indicates a 50% cutpoint of about 0.4 μm.

Figure 6:
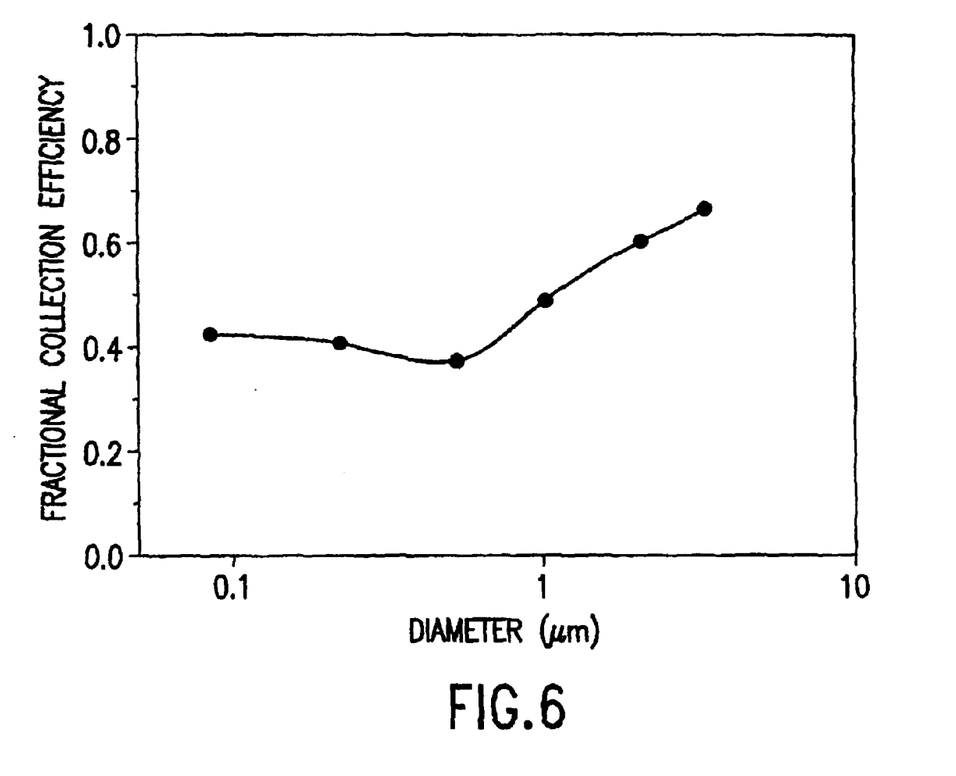
FIG. 6 is a diagram showing collection efficiency vs. particles size for the entire system.

The collection efficiency for the entire system 58 (i.e., steam injectors, condensers, virtual impactor, real impactor, and transfer lines to the fraction collector) was measured using PSL particles (0.1 to 3 μm) and is shown in FIG. 6. For input particles <0.5 μm, the collection efficiency is about 40% and is independent of particle size. For particles >0.5 μm, the collection efficiency gradually increases with size to 68% for 2.977 μm input particles. The lower efficiency for small particles is due to incomplete growth of those particles, as seen in FIG. 3.

A mass balance for particle collection and loss performed for 0.084 μm particles through the entire condensational growth system is shown in a summarized manner in Table 2. Each component was washed before and after the tests to determine losses. The overall collection efficiency for the grown droplets was 32%, with the virtual impactor major flow and condensers being the major sources of loss, accounting for 26% and 25% of the input particles, respectively. Based on ambient concentrations measured in College Park, Md., a non-industrial suburb of Washington, D.C., average aqueous system blanks (Al, 3; As, 0.06; Cd, 0.03; Cr, 0.4; Cu, 0.2; Fe, 1.5; Mn, 0.4; Ni, 0.1; Pb, 0.4; Sb, 0.3; Se, 0.08; and Zn, 1.2 ng ML$^{-1}$) are adequate to achieve average sample-to-blank ratios ranging from >3 to >30 for all but Cr and Ni (for which S:B ratios are in the range of 1 to 5) in the current system.

TABLE 2

Mass balance for condensational growth and collection of 0.084 μm particles.

| Collected | |
|---|---|
| Real impactor | 32% |
| Lost | |
| Virtual impactor major flow | 26% |
| Condensers | 25% |
| Transport to real impactor | 9% |
| Within virtual impactor | 6% |
| Penetration of real impactor | 2% |
| Total | 100% |

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A system for multi-element substantially real time chemical analysis of aerosol particles, comprising:

a particle concentrator unit having an input for receiving initial particle-laden air flow at the flow rate in the approximate range 170–260 L/min and an output for discharging therefrom a concentrated air flow containing droplets obtained by condensational growth of said initial particles, a real impactor having an inlet and an outlet, said real impactor receiving at said inlet thereof said concentrated air flow from said particle concentrator unit and discharging from said outlet thereof a liquid slurry containing said droplets, and means for multi-element analysis of said liquid slurry received from said real impactor.

2. The system of claim 1, further comprising a fraction collector coupled to said outlet of said real impactor, said fraction collector including a plurality of sample vials for filling said liquid slurry into at least one sample vial for an off-line analysis by said means for multi-element analysis.

3. The system of claim 1, wherein said outlet of said real impactor is directly coupled to means for multi-element analysis for on-line analysis.

4. The system of claim 1, wherein said particle concentration unit includes:

a saturator receiving said initial particle-laden air flow and a stream flow, and discharging a saturated said particle-laden air flow containing said initial particles, a condenser coupled to said saturator for receiving said saturated particle-laden air flow and condensationally growing said initial particles in diameter thereof to produce said droplets, and a virtual impactor coupled to said condenser for receiving therefrom the air flow laden with said droplets and for separating therefrom the droplets exceeding a predetermined diameter thereby obtaining said concentrated air flow containing said droplets.

5. The system of claim 1, further comprising a steam generator producing a flow of steam supplied to said saturator.

6. The system of claim 1, wherein said flow rate of said air flow is approximately 200 L/min.

7. The system of claim 5, wherein said flow of steam is supplied to said saturator at the flow rate not exceeding 6 L/min.

8. A The system of claim 4, further comprising a controllable heater coupled to said saturator to heat the same to a predetermined temperature.

9. The system of claim 4, further comprising cooling means coupled to said condenser for maintaining walls thereof at a predetermined temperature.

10. The system of claim 9, wherein said predetermined temperature of the walls of said condenser is in the approximate range of 0.5°–10° C.

11. The system of claim 6, wherein the flow rate of the air flow laden with droplets received at said virtual impactor is approximately 170 L/min.

12. The system of claim 4, wherein said virtual impactor divides said air flow into (a) a minor flow of air from said air flow, said minor flow of air containing said droplets exceeding the predetermined diameter, and (b) a major flow of air.

13. The system of claim 12, wherein said minor flow of air is supplied to said real impactor with the approximate flow rate of 10 L/min.

14. The system of claim 12, wherein said major flow exits said virtual impactor with the flow rate of approximately 190 L/min.

15. The system of claim 1, wherein said means for multi-element analysis includes Graphite Furnace Atomic Absorption Analyzer.

16. The system of claim 4, wherein said predetermined diameter is within the approximate range of 0.7–12 $\mu$m.

17. The system of claim 2, wherein said liquid slurry is expelled from said real impactor approximately every 30 minutes.

18. The system of claim 4, wherein a residence time of said droplets within said condenser is in the range 0.03 sec.–0.6 sec.

19. A method of multi-element analysis of aerosol particles, comprising the steps of:

supplying a flow of ambient air laden with initial particles to a saturator at the flow rate in the approximate range 170–260 L/min, injecting a flow of steam to said saturator for being mixed with said ambient air and for saturating the same, directing the saturated ambient air from said saturator into a condenser for condensational growth of said initial particles thereby producing an air flow laden with droplets of a diameter larger than diameters of said initial particles, supplying said air flow laden with said droplets to a virtual impactor, for separating from said air flow a concentrated air flow containing said droplets exceeding a predetermined diameter, directing said concentrated air flow from said virtual impactor to a real impactor for forming a liquid slurry containing said droplets of said exceeding diameter, and exposing said liquid slurry to a multi-element analysis.

20. The method of claim 19, wherein said liquid slurry is delivered to a sample vial prior to said multi-element analysis for off-line analyses.

21. The method of claim 19, wherein said liquid slurry is supplied directly from said real impactor to a multi-element analysis means for on-line analyses.

22. The method of claim 19, wherein said liquid slurry is analyzed by a graphite furnace absorption spectrometer.

* * * * *